United States Patent [19]

Fitzig et al.

[11] Patent Number: 4,930,920
[45] Date of Patent: Jun. 5, 1990

[54] COMBINED MATERIAL APPLICATOR AND GINGIVAL TISSUE RETRACTOR FOR MAKING DENTAL IMPRESSIONS

[75] Inventors: Simon Fitzig, Tel Aviv; David Feder, Kfar Saba, both of Israel

[73] Assignee: Raniot University Authority of Applied Research & Industrial Development Ltd., Tel-Aviv, Israel

[21] Appl. No.: 229,953

[22] Filed: Aug. 9, 1988

[30] Foreign Application Priority Data

Aug. 10, 1987 [IL] Israel .......................................... 83489

[51] Int. Cl.⁵ ............................ B67D 5/00; A61C 9/00
[52] U.S. Cl. ......................................... 401/176; 433/89
[58] Field of Search .................. 433/3, 78, 80, 81, 82, 433/83, 89, 90, 93, 94, 180, 326, 229; 604/38, 116, 117, 162, 192, 218, 261, 264, 268, 289, 294, 300, 302, 311; 128/62 A, 67, 776, 777; 401/48, 139, 137, 176, 193, 261, 265-267

[56] References Cited

U.S. PATENT DOCUMENTS

| | | | |
|---|---|---|---|
| 953,022 | 3/1910 | Dollin et al. | 433/89 |
| 1,033,819 | 7/1912 | McMann | 433/89 |
| 1,568,347 | 1/1926 | Shaw | 401/48 |
| 2,837,824 | 6/1958 | Moller | 433/90 |
| 3,221,409 | 12/1965 | Thiel et al. | 433/90 X |
| 3,827,147 | 8/1974 | Condon | 433/90 |
| 3,872,866 | 3/1975 | Lelicoff | 604/302 |
| 4,627,834 | 12/1986 | Lee | 604/117 X |

FOREIGN PATENT DOCUMENTS

| | | | |
|---|---|---|---|
| 0090961 | 10/1983 | European Pat. Off. | 433/89 |
| 2477408 | 9/1981 | France | 433/89 |
| 8105902 | 7/1983 | Netherlands | 433/89 |
| 691703 | 5/1953 | United Kingdom | 433/89 |

*Primary Examiner*—Richard J. Apley
*Assistant Examiner*—David F. Crosby
*Attorney, Agent, or Firm*—Benjamin J. Barish

[57] ABSTRACT

An applicator particularly useful in making dental impressions, includes a barrel for containing a dental impression material, an ejector nozzle fixed to the barrel at one end through which the dental impression material is to be ejected, a plunger movable through the opposite end of the barrel for ejecting the dental impression material through the ejector nozzle, and a retractor adjacent to the tip of the ejector nozzle for retracting the gingival tissue at the time the dental impression material is ejected.

13 Claims, 1 Drawing Sheet

COMBINED MATERIAL APPLICATOR AND GINGIVAL TISSUE RETRACTOR FOR MAKING DENTAL IMPRESSIONS

BACKGROUND OF THE INVENTION

The present invention relates to an applicator for ejecting material, and particularly to an applicator useful for use in ejecting dental impression material for making dental impressions.

Dental impression for cast restorations is often a very difficult procedure, especially when the tooth preparation finishing lines extend subgingivally, i.e., below the gum line. This is often the case where consideration has to be given to esthetics, retention, extent of carious destruction, and the like. To overcome the problem of replication of the subgingival area, different techniques have been employed for allowing the impression material to be carried to the bottom of the gingival pocket. These techniques include electrosurgery, copper band impressions, and the use of gingival retraction cords combined with the use of a syringe. However, these known techniques are time-consuming and often involve traumatizing of the gingival tissues, frequently causing bleeding. Such bleeding complicates the impression taking, often requiring the dentist to discontinue further work until the bleeding has stopped.

This bleeding has also an undesirable risk of infecting the dental personnel with blood-borne diseases, such as Hepatitis B or AIDS (Acquired Immune Deficiency Syndrome). In fact, it is known that doctors and dentists are infected by the Hepatitis B virus at a rate two or three times that of the public at large. This creates a high degree of apprehension on the part of the medical or dental personnel treating the patient, and may also affect the attitude and/or service of such personnel with respect to the patient in view of the possibility of infection by the patient.

An object of the present invention is to provide an applicator particularly useful in making dental impressions which reduces or avoids the above drawbacks.

BRIEF SUMMARY OF THE INVENTION

According to the present invention, there is provided an applicator particularly useful in making a dental impression of a tooth, comprising: a barrel for containing a dental impression material; an ejector nozzle fixed to the barrel at one end thereof through which the dental impression material is to be ejected; a plunger movable through the opposite end of the barrel for ejecting the dental impression material through the ejector nozzle; and a retractor at the one end of the barrel adjacent to the tip of the ejector nozzle and including an arm engageable with the gingival tissue at the tooth whose impression is to be made for retracting the gingival tissue at the time the dental impression material is ejected.

It will thus be seen that the applicator permits retraction of the gingival tissue at the time of ejection of the dental impression material. Accordingly, the applicator enables very precise impressions to be taken especially when the tooth preparation finishing lines extend subgingivally, without the need for electrosurgery, copper band impressions, or gingival retraction cords. The applicator is therefore not only time-saving and hygenic, but also produces less traumatizing of the gingival tissue, and thereby less likelihood of bleeding.

In the preferred embodiment of the invention described below, the retractor comprises an arm secured to the one end of the barrel and terminating in a substantially spherical tip located adjacent to the tip of the ejector nozzle; in the illustrated embodiment, the arm of the retractor extends substantially parallel to the ejector nozzle.

According to a further feature in the described preferred embodiment, the barrel is formed on its outer surface with an annular rib extending circumferentially around the barrel to facilitate manually rotating the barrel, its ejector nozzle, and the retractor, at the time the dental impression material is ejected through the ejector nozzle.

According to a further feature, the ejector nozzle and the retractor are both slightly curved away from the longitudinal axis of the barrel.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

Figure 1:
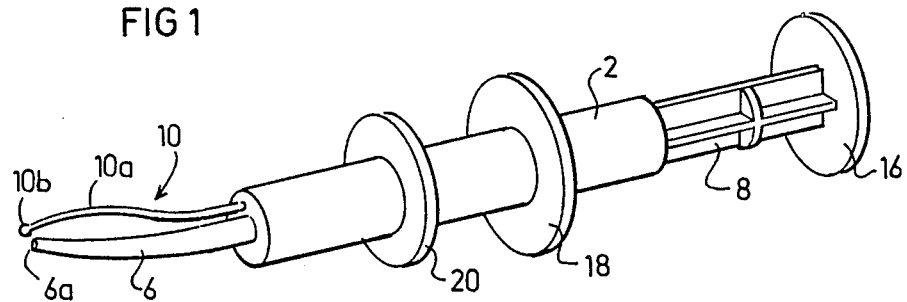
FIG. 1 is a side elevational view illustrating one form of applicator constructed in accordance with the present invention.

The applicator illustrated in the drawings is particularly useful for ejecting a dental impression (e.g., an elastomer) material for making dental impressions where the tooth preparation finishing lines extend subgingivally. The applicator comprises a barrel 2 formed with an internal chamber 4 for containing the dental impression material; an ejector nozzle 6 at one end of the barrel through which the dental impression material is to be ejected; and a plunger 8 at the opposite end of the barrel for ejecting the dental impression material through the ejector nozzle. The illustrated applicator further includes a retractor, generally designated 10, at the end of the barrel 2 adjacent to the ejector nozzle 6 for retracting the gingival tissue at the time the dental impression material is ejected.

More particularly, the barrel 2, nozzle 6 and plunger 8 may be of similar construction as in a conventional syringe. Thus, plunger 8 is formed with a stem 12 terminating in a piston 14 movable within the barrel and defining the chamber 4 containing the dental impression material to be ejected upon moving the plunger 8 towards the ejector nozzle. To facilitate moving the plunger 8, it is formed with an enlarged end wall 16, and the outer surface of barrel 2 is formed with an annular wall 18, such that wall 16 is engageable by the thumb of the user while wall 18 is engageable by two fingers of the user to move the plunger towards the ejector nozzle.

The outer surface of barrel 2 is formed with an annular rib 20 of circular configuration extending circumferentially around the barrel. Rib 20 facilitates manually rotating the barrel, its ejector nozzle 6, and also the retractor 10, at the time the dental impression material is injected through the ejector nozzle.

Ejector nozzle 6 is of elongated tapered configuration extending generally axially of barrel 2 but curved slightly away from the longitudinal axis of the barrel. In addition, retractor 10 includes an arm 10a extending generally parallel to ejector nozzle 6, the arm terminating in a substantially spherical tip 10b located adjacent to the tip 6a of the ejector nozzle. Arm 10a should be very rigid, e.g., of metal.

Figure 2:
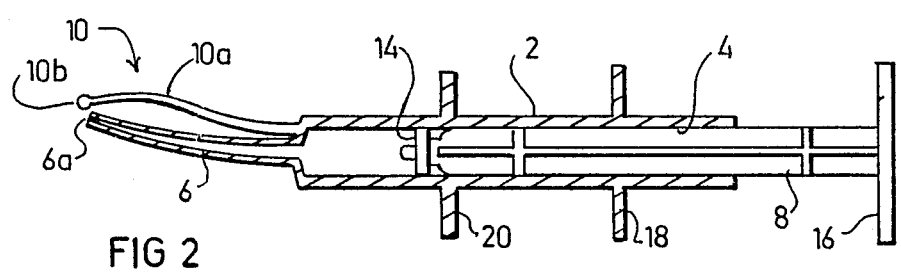
FIG. 2 is a longitudinal sectional view illustrating the applicator of FIG. 1.
Figure 3:
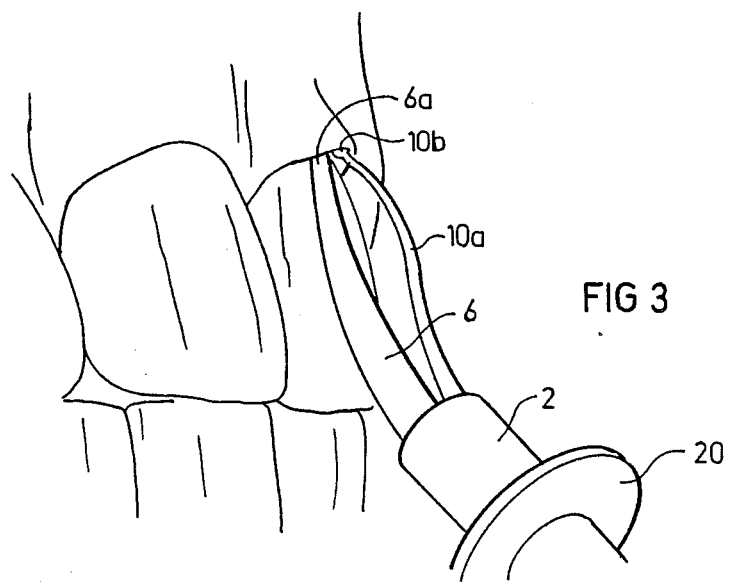
FIG. 3 illustrates the manner of using the applicator of FIG. 1 for making dental impressions.

The manner of using the applicator illustrated in FIGS. 1 and 2 will be apparent from FIG. 3. Thus, with the plunger 16 removed, chamber 4 within the barrel 2 is filled with the dental impression material, and then plunger 16 is inserted into the end of the barrel. The dentist then uses the applicator for retracting the gingival tissue simultaneously with the ejection of the dental impression material. For this purpose, the dentist applies both the tip 6a of the ejector nozzle 6 and the spherical tip 10b of the retractor 10, between the gingival tissue and the tooth so as to retract the gingival tissue from the tooth, and to open the sulcus, while the dental impression material is ejected via nozzle 6 by pressing end wall 16 of the plunger towards annular wall 18 of the barrel. During this procedure, the dentist may rotate the barrel 2 via circular rib 20 to position the spherical tip 10b of the retractor 10, and the tip 6a of the ejector nozzle 6, as required in order to produce precise impressions.

It will be appreciated that retractor 10 could be constructed as an integral part of barrel 2 together with the ejector nozzle 6; alternatively, it could be constructed as an attachment for application to the barrel. The applicator, and particularly retractor 10, may be made in a number of different sizes to suit different cases with varying gingivi.

Many other variations, modifications and applications of the invention will be apparent.

What is claimed is:

1. An applicator particularly useful in making a dental impression of a tooth, comprising: a barrel for containing a dental impression material; an ejector nozzle fixed to the barrel at one end thereof through which the dental impression material is to be ejected; a plunger movable through the opposite end of the barrel for ejecting the dental impression material through the ejector nozzle; and a retractor at said one end of the barrel adjacent to the tip of said ejector nozzle and including an arm secured to said one end of the barrel and terminating in a substantially spherical tip located adjacent to the tip of the ejector nozzle and engageable with the gingival tissue at the tooth whose impression is to be made for retracting the gingival tissue at the time the dental impression material is ejected.

2. The applicator according to claim 1, wherein said arm of the retractor extends substantially parallel to said ejector nozzle.

3. The applicator according to claim 1, wherein said barrel is formed on its outer surface with an annular rib extending circumferentially around the barrel to facilitate manually rotating the barrel, its ejector nozzle, and the retractor, at the time the dental impression material is ejected through the ejector nozzle.

4. The applicator according to claim 1, wherein said ejector nozzle and said retractor are both slightly curved away from the longitudinal axis of the barrel.

5. The applicator according to claim 1, wherein the barrel and the end of said plunger are each formed with an annular wall, the wall of the barrel being engageable by two fingers of the user, and the wall of the plunger being engageable by the thumb of the user, for moving said plunger inwardly of the barrel for ejecting the dental impression material through the ejector nozzle.

6. An applicator particularly useful in making dental impressions, comprising: a barrel for containing a dental impression material; an ejector nozzle fixed to the barrel at one end thereof through which the dental impression material is to be ejected; means for ejecting the dental impression material through the ejector nozzle; and a retractor at said one end of the barrel adjacent to the tip of said ejector nozzle for retracting the gingival tissue at the time the dental impression material is ejected; said retractor comprising an arm secured to said one end of the barrel and extending substantially parallel to said ejector nozzle, and a substantially spherical tip located adjacent to the tip of the ejector nozzle.

7. The applicator according to claim 6 wherein said barrel is formed on its outer surface with an annular rib extending circumferentially around the barrel to facilitate manually rotating the barrel, its ejector nozzle, and the retractor, at the time the dental impression material is ejected through the ejector nozzle.

8. The applicator according to claim 6, wherein said ejector nozzle and said retractor are both slightly curved away from the longitudinal axis of the barrel.

9. The applicator according to claim 6, wherein said means for ejecting the dental impression material through the ejector nozzle comprises a plunger, and wherein the barrel and the end of said plunger are each formed with an annular wall, the wall of the barrel being engageable by two fingers of the user, and the wall of the plunger being engageable by the thumb of the user, for moving said plunger inwardly of the barrel for ejecting the dental impression material through the ejector nozzle.

10. An applicator particulary useful in making dental impressions, comprising: a barrel for containing a dental impression material; an ejector nozzle fixed to the barrel at one end thereof through which the dental impression material is to be ejected; a plunger movable through the opposite end of the barrel for ejecting the dental impression material through the ejector nozzle; and a retractor at said one end of the barrel adjacent to the tip of said ejector nozzle for retracting the gingival tissue at the time the dental impression material is ejected; said ejector nozzle and said retractor both being slightly curved away from the longitudinal axis of the barrel, said retractor comprising an arm secured to said one end of the barrel and terminating in a substantially spherical tip located adjacent to the tip of the ejector nozzle.

11. The applicator according to claim 10, wherein said arm of the retractor extends substantially parallel to said ejector nozzle.

12. The applicator according to claim 10, wherein said barrel is formed on its outer surface with an annular rib extending circumferentially around the barrel to facilitate manually rotating the barrel, its ejector nozzle, and the retractor, at the time the dental impression material is ejected through the ejector nozzle.

13. The applicator according to claim 10, wherein the barrel and the end of said plunger are each formed with an annular wall, the wall of the barrel being engageable by two fingers of the user, and the wall of the plunger being engageable by the thumb of the user, for moving said plunger inwardly of the barrel for ejecting the dental impression material through the ejector nozzle.

* * * * *